United States Patent
Adachi et al.

(10) Patent No.: US 8,945,646 B2
(45) Date of Patent: Feb. 3, 2015

(54) METHOD FOR MANUFACTURING POLYMETHOXYFLAVONES THAT ARE HIGHLY STABLE OVER TIME AND HAVE REDUCED RESIDUAL PESTICIDE LEVELS

(75) Inventors: Kenji Adachi, Chiba (JP); Tsuyoshi Arima, Chiba (JP); Shuichi Muranishi, Chiba (JP)

(73) Assignee: Ogawa & Co., Ltd., Tokyo (JP)

( * ) Notice: Subject to any disclaimer, the term of this patent is extended or adjusted under 35 U.S.C. 154(b) by 0 days.

(21) Appl. No.: 13/575,823

(22) PCT Filed: Jan. 29, 2010

(86) PCT No.: PCT/JP2010/051231
§ 371 (c)(1),
(2), (4) Date: Jul. 27, 2012

(87) PCT Pub. No.: WO2011/092840
PCT Pub. Date: Aug. 4, 2011

(65) Prior Publication Data
US 2012/0301596 A1    Nov. 29, 2012

(51) Int. Cl.
| A23L 1/222 | (2006.01) |
| A23L 1/30 | (2006.01) |
| A23L 2/52 | (2006.01) |
| A23L 2/56 | (2006.01) |
| A61K 31/352 | (2006.01) |
| C07D 311/30 | (2006.01) |

(52) U.S. Cl.
CPC .............. *A23L 1/3002* (2013.01); *A23L 1/2225* (2013.01); *A23L 2/52* (2013.01); *A23L 2/56* (2013.01); *C07D 311/30* (2013.01); *A61K 31/352* (2013.01)
USPC ........ 426/330.5; 426/429; 426/478; 426/534; 426/536

(58) Field of Classification Search
None
See application file for complete search history.

(56) References Cited

U.S. PATENT DOCUMENTS

| 3,847,899 A | * | 11/1974 | Mitchell ........................ 536/8 |
| 5,580,545 A | | 12/1996 | Washino et al. |
| 8,435,586 B2 | * | 5/2013 | Krammer et al. ............. 426/536 |

FOREIGN PATENT DOCUMENTS

| JP | 6-335362 | | 12/1994 |
| JP | 11-169148 | | 6/1999 |
| JP | 2000-72790 | | 3/2000 |
| JP | 2003-292488 | | 10/2003 |
| JP | 2003292488 | * | 10/2003 |
| JP | 2004-210682 | | 7/2004 |
| JP | 2004-223346 | | 8/2004 |
| JP | 2006-89414 | | 4/2006 |
| JP | 2007-286041 | | 11/2007 |
| JP | 2008-272594 | | 11/2008 |
| JP | 2008-280282 | * | 11/2008 |
| JP | 2009-511643 | | 3/2009 |
| JP | 2009-215318 | * | 9/2009 |
| JP | 2009-533494 | | 9/2009 |
| JP | 2010-037317 | * | 2/2010 |
| JP | 2010-37317 | | 2/2010 |
| WO | WO 2009/057633 A1 | | 5/2009 |

OTHER PUBLICATIONS

International Search Report issued Mar. 2, 2010 in Application No. PCT/JP2010/051231.
English Translation of International Preliminary Report on Patentability and Written Opinion issued Aug. 9, 2012 in Application No. PCT/JP2010/051231.
Nippon Nogeikagaku Kaishi, vol. 75, No. 12, 2001, pp. 1283-1290.
Kouryou Kagaku Soran (I), Hirokawa Shoten, 1967, p. 232.
Kajitsu no Kagaku, Asakura Publishing, 1991, p. 130.
Y. Eguchi, et al., "Factory Operation Series: Absorption", 1st edition, Jul. 1, 1975, pp. 84-97 and 222-225.
Office Action issued on Jul. 2, 2013 in the counterpart Japanese Application No. 2008-205527 (with its abridged English Translation).

* cited by examiner

*Primary Examiner* — Carolyn Paden
(74) *Attorney, Agent, or Firm* — Oblon, Spivak, McClelland, Maier & Neustadt, L.L.P.

(57) ABSTRACT

There is provided a method for manufacturing inexpensive, highly safe, highly stable, versatile polymethoxyflavones that can be used in food products and easily incorporated into a variety of pharmaceutical formulations, whereby in one pass, a large quantity of polymethoxyflavones can be isolated from other components in citrus peel oil, as well as a method for its use. The method for manufacturing polymethoxyflavones from citrus plant peel oil comprises a step of removing the volatile components in citrus plant peel oil by distillation to obtain a distillation residue, a step of distilling the residue with a thin-film vacuum distillation apparatus to obtain a fraction, a step of extracting the fraction with an aqueous ethanol solution to obtain an extract, and a step of contacting active carbon with the extract after removal of the insoluble oils in the extract for refining, as a method for manufacturing polymethoxyflavones that are highly stable over time and have reduced residual pesticide levels.

13 Claims, No Drawings

METHOD FOR MANUFACTURING POLYMETHOXYFLAVONES THAT ARE HIGHLY STABLE OVER TIME AND HAVE REDUCED RESIDUAL PESTICIDE LEVELS

TECHNICAL FIELD

The present invention relates to a simple method for manufacturing naturally derived polymethoxyflavones.

Specifically, it relates to a method for manufacturing polymethoxyflavones from peel oil of citrus plants, comprising a step of removing the volatile components in citrus plant peel oil by distillation to obtain a distillation residue, a step of distilling the residue with a thin-film vacuum distillation apparatus to obtain a fraction, a step of extracting the fraction with an aqueous ethanol solution to obtain an extract, and a step of contacting active carbon with the extract after removal of the insoluble oils in the extract for refining, as a method for manufacturing polymethoxyflavones that are highly stable over time and have reduced residual pesticide levels.

According to this method it is possible to efficiently produce polymethoxyflavones at low cost in a short period of time without using organic solvents or the like.

BACKGROUND ART

Polymethoxyflavones represented by the structural formula shown in the following formula (I) are known in the prior art to be abundantly present in citrus plants, and specifically citrus peels.

[Chemical Formula 1]

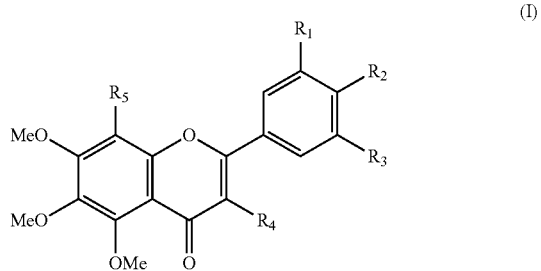

(I)

(In the formula, $R_1$, $R_2$, $R_3$, $R_4$ and $R_5$ each independently represent hydrogen or methoxy.)

In particular, nobiletin (a compound of formula (I) wherein $R_1$, $R_2$, $R_3$, $R_4$ and $R_5$ are all methoxy groups) is a substance with established physiological activity, including an anticarcinogenic effect (Non-patent document 1).

In the field of foods as well, polymethoxyflavones are attracting attention for their various useful effects that have been discovered, as taste-improving agents and in taste-improving methods (Patent document 1), or as flavor deterioration inhibitor (Patent document 2).

Citrus plant peel oil contains, in addition to polymethoxyflavones, also numerous different kinds of components with widely varying properties (see Non-patent document 2 and Non-patent document 3, for example). For example, it contains volatile components, including hydrocarbon compounds such as terpenes, carbonyl compounds such as aldehydes and esters, or alcohols, and non-volatile components such as waxes and carotenoid pigments that do not volatilize under ordinary conditions, and it is therefore considered difficult to selectively separate polymethoxyflavones by convenient methods.

As prior art methods for producing polymethoxyflavones from citrus plant peel oil there have been proposed a method of hot extraction of a starting material of Rutaceae plant fruit, peel, peel oil, leaves or the like, using an organic solvent such as methanol, ethanol or chloroform, and a method of extraction using a supercritical fluid solvent (Patent document 1, Patent document 2).

In these methods, however, it has not been possible to obtain highly pure polymethoxyflavones from starting materials that contain hydrocarbon compounds, carbonyl compounds, esters and alcohols, such as limonene, linalool, geraniol, nerol, α-terpineol and citral, and other fragrance components, as well as pigment components such as carotenoids, in addition to polymethoxyflavones. Thus, when polymethoxyflavones obtained by conventional extraction methods are to be used as taste-improving agents or flavor deterioration retarders, their uses have been very restricted due to problems such as altered flavor, off-odor and coloration, caused by contaminants in the extract.

In order to obtain highly pure polymethoxyflavones, therefore, prior art techniques have involved loading an extract containing polymethoxyflavones into a column packed with a support such as silica gel, aluminum oxide, alkylsilylated silica gel, allylsilylated silica gel or the like, and performing separation and refining by column chromatography or high-performance liquid chromatography using a developing solvent such as ethyl acetate-hexane or water-acetonitrile. Liquid-liquid partition chromatography using hexane or pentane and aqueous methanol or ethanol is also sometimes used.

However, the polymethoxyflavones obtained by these methods, while having extremely high purity, are difficult to separate and purify as large amounts of polymethoxyflavones in a single procedure. In addition, long periods of time are required to prepare large amounts of polymethoxyflavones, while highly expensive organic solvents and special equipment are also necessary, making it impossible to avoid increased costs, and therefore such methods are considered unsuitable for industrial production. Moreover, these methods employ organic solvents that can have adverse effects on the human body, such as n-hexane, ethyl acetate, tetrahydrofuran and acetonitrile, and therefore the use of the obtained polymethoxyflavones in food products is inadequate from a safety standpoint.

A simple method for separating polymethoxyflavones has been proposed, as a method in which extraction is performed with an alcoholic aqueous solution from the residue after distillation removal of the volatile components from citrus plant peel oil (Patent document 3). This method allows compositions with high methoxyflavone contents to be obtained by a simple procedure from blackish brown distillation tar residue, but while it can be used directly as an aqueous formulation, precipitates are produced over time and the stability is lacking. In addition, the compositions lack general utility as formulations other than aqueous formulations. That is, when the solvent has been distilled off from the alcohol solution, the methoxyflavone composition solidifies into hard form making it difficult to handle, and this has hampered efforts to prepare oil-soluble formulations and powdered formulations.

Residual pesticides are another problem to be considered when separating polymethoxyflavones at high concentrations from citrus plant peel.

Most citrus plants are administered pesticides or antiseptic agents during cultivation or after harvest for purposes of prevention and measures against insect damage or disease, facilitating insect removal or weed removal, and for prolonged storage of fruit. The administered pesticides and antiseptic agents are removed by rinsing the harvested fruit, but portions remain on the peels, and can potentially be extracted into the peel oil when essential oils are pressed from the peels.

Examples of residual pesticides detected on citrus fruits and bananas imported into Japan include organic chlorine-based pesticides (chlorobenzilate and dicofol), organic phosphorus-based pesticides (pyridaphenthion and methidathion), and pyrethroid-based pesticides (cypermethrin and fenpropathrin).

Most pesticides and antiseptic agents are non-volatile components, and can potentially be concentrated during the refining steps for polymethoxyflavones.

As a method for removing pesticides from plant extracts there is known, for example, (1) a method of dissolution in a liquid mixture of a lower aliphatic alcohol and water at a volume ratio of between 10:90 and 80:20, and passing the obtained solution through a column packed with a porous adsorption resin with a most frequent pore radius of 30-120 angstrom, to absorb the residual pesticides in the solution onto the adsorption resin, and then recovering the plant extract from the solution after treatment (Patent document 4). There is also known (2) a method of contacting a plant extract with a carbon dioxide gas fluid in the supercritical to subcritical state to remove the residual pesticides (Patent document 5).

However, since long periods of time are required for passage through the column in method (1) it is not possible to treat large amounts of extract, while highly expensive organic solvents and special equipment are also necessary, making it impossible to avoid increased costs, and therefore such a method is considered unsuitable for industrial production. Moreover, while it is suitable for removal of organic chlorine-based residual pesticides such as BHC and DDT, it lacks general utility, and the extraction components with properties similar to those of the residual pesticides are lost by adsorption, and the extract yield is reduced.

On the other hand, method (2) allows efficient removal of residual pesticides from plant extracts without loss or degradation of the plant extraction components, but it requires special equipment and is therefore very costly.

Different methods known for removal of pesticides from essential oils include (3) a method of contacting with a strong cation-exchange resin or a strong anion-exchange resin (Patent document 6) and a method of contacting with an aqueous alkali solution (Patent document 7).

However, method (3), while allowing selective removal of basic, acidic and neutral organic compounds, lacks general utility in cases of residue of pesticides with various different physical properties.

Thus, no known method has yet been successfully developed for production of polymethoxyflavone compositions from citrus plant peel oils, that can be used for food products without safety concerns, is convenient and economically advantageous, and has general utility, and therefore a new manufacturing method is desired.

CITATION LIST

Patent Literature

[Patent document 1] Japanese Unexamined Patent Application Publication HEI No. 6-335362
[Patent document 2] Japanese Unexamined Patent Application Publication HEI No. 11-169148
[Patent document 3] Japanese Unexamined Patent Application Publication No. 2003-292488
[Patent document 4] Japanese Unexamined Patent Application Publication No. 2000-72790
[Patent document 5] Japanese Unexamined Patent Application Publication No. 2006-89414
[Patent document 6] Japanese Patent Public Inspection No. 2009-511643
[Patent document 7] Japanese Patent Public Inspection No. 2009-533494

Non-Patent Literature

[Non-patent Document 1] Nippon Nogeikagaku Kaishi, Vol. 75, No. 12, 2001, p. 1283-1290
[Non-patent Document 2] Kouryou Kagaku Soran (I), p. 232, Hirokawa Shoten, 1967
[Non-patent Document 3] Kajitsu no Kagaku, p. 130, Asakura Publishing, 1991

SUMMARY OF INVENTION

Technical Problem

It is an object of the invention to solve the problems of the prior art described above, by providing a method for manufacturing a polymethoxyflavone composition that allows separation of large amounts of inexpensive, highly safe, highly stable and versatile polymethoxyflavones that can be used in food products, at one pass from other components in citrus plant peel oil.

Citrus plant peel oil, and especially orange peel oil, to be used as the starting material, is utilized in large amounts industrially as an aromatic material for terpenes such as limonene, or essential oils from which the terpenes have been removed (terpeneless oils), and the residues are currently discarded for the most part, without being effectively utilized. However, polymethoxyflavones are present in large amounts in the residues that remain after obtaining aromatics such as limonene, and the invention can be applied as a starting material with nearly no additional cost, which also contributes toward the purpose of effective utilization of waste.

Solution to Problem

The present inventors have focused on the fact that polymethoxyflavones have various effects including physiological activity and taste-improving effects, and have conducted diligent research on methods for convenient and efficient separation thereof, and as a result we have completed this invention upon finding that if the residue obtained after removing the volatile components such as terpene compounds from citrus plant peel oil, or the fraction obtained by distillation of the residue with a thin-film vacuum distillation apparatus, is extracted with an aqueous ethanol solution and contacted with active carbon after removal of the insoluble oils, it is possible to produce high-purity polymethoxyflavones with high stability over time and reduced residual pesticide content, at low cost and in a very convenient manner.

That is, the invention is a method for manufacturing polymethoxyflavones wherein the fraction of a residue obtained after removing the volatile component from citrus plant peel oil by distillation as necessary, obtained by distillation of the residue with a thin-film vacuum distillation apparatus, is extracted with an aqueous ethanol solution, removed of its insoluble oils and contacted with active carbon.

Specifically, the starting material citrus plant is one or more selected from among sweet orange (*Citrus sinensis*), sour orange (*Citrus aurantium*), tangerine (*Citrus reticlata* Blanco var. *tangerine*), mandarin (*Citrus reticlata* Blanco var. *mandarin*) and shekwasha (*Citrus depressa* Hayata), and more specifically, the removal step by first distillation of the volatile components is performed under conditions with a pressure of 1-100 Pa and a temperature of 120° C. to 220° C., the second distillation step with a thin-film vacuum distillation apparatus is performed under conditions with a pressure of 0.4-2 Pa and a temperature of 190° C. to 260° C., and the extraction step with an aqueous ethanol solution is performed with an ethanol concentration of 10-50% and contact of the aqueous ethanol solution with active carbon.

Also, the polymethoxyflavones are at least one or more selected from the group consisting of compounds represented by the following formula (I):

[Chemical Formula 2]

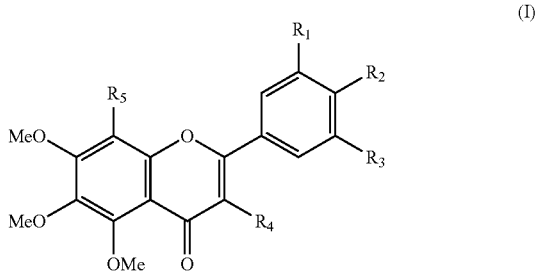

(I)

(wherein $R_1$, $R_2$, $R_3$, $R_4$ and $R_5$ each independently represent hydrogen or methoxy groups), and more specifically the polymethoxyflavones are among pentamethoxyflavone, nobiletin, tetramethoxyflavone, tangeretin and heptamethoxyflavone.

The invention is also a polymethoxyflavone composition comprising at least 70 wt % and preferably at least 80 wt % of polymethoxyflavones produced by the manufacturing method, and an oral composition comprising the polymethoxyflavone composition.

Advantageous Effects of Invention

According to the invention it is possible to provide a method for manufacturing inexpensive, highly safe, highly stable, versatile polymethoxyflavones that can be used in food products, the method allowing separation of large amounts of highly pure polymethoxyflavones at one pass from other components in citrus plant peel oil, which is a readily available starting material.

The polymethoxyflavones have high purity, while the amounts of residual pesticides are notably reduced by the activated carbon treatment.

DESCRIPTION OF EMBODIMENTS

The present invention is a method for manufacturing polymethoxyflavones that are highly stable over time and have reduced residual pesticide levels, the method comprising (a) a step of removing the volatile components in citrus plant peel oil by distillation to obtain a distillation residue, (b) a step of distilling the residue with a thin-film vacuum distillation apparatus to obtain a fraction, (c) a step of extracting the fraction with an aqueous ethanol solution to obtain an extract, and (d) a step of contacting active carbon with the extract after removal of the insoluble oils in the extract for refining.

The formulation comprising the polymethoxyflavones of the invention may be a water-soluble formulation, oil-soluble formulation or powder formulation, depending on the purpose of use.

The solvent to be used in a water-soluble formulation of the invention may be a (mixed) solvent of water, an alcohol, glycerin, propylene glycol, triethyl citrate or the like, with dissolution to a suitable concentration to prepare the formulation. From the viewpoint of stability of the formulation, a mixed solvent of water and ethanol is preferred.

An oil-soluble formulation of the invention is used by dissolution or dispersion in an edible fat or oil. The edible fat or oil to be used for the invention is not particularly restricted, and examples include animal or plant-derived fats and oils such as avocado oil, sardine oil, olive oil, cocoa butter, kapok oil, poppy seed oil, burdock oil, sesame oil, rice bran oil, wheat germ oil, mackerel oil, saury pike oil, beef tallow, soybean oil, cod liver oil, evening primrose oil, camellia oil, corn oil, rapeseed oil, babassu oil, palm oil, palm kernel oil, mallow oil, cottonseed oil, menma oil, coconut oil, peanut oil and lard, as well as these oils and fats in refined forms or hydrogenated forms, with medium chain fatty acid triglycerides being preferred from the viewpoint of stability of the formulation.

An emulsifier to be used in a powder formulation of the invention is not particularly restricted so long as it is an emulsifier, and examples include gum arabic, chemically modified starch, tragacanth gum, guar gum, karaya gum, xanthan gum, pectin, alginic acid and its salts, carrageenan, microcrystalline cellulose and the like, with gum arabic being preferred from the viewpoint of ease of formulation and stability.

The form of a food product containing a polymethoxyflavone of the invention may be capsules, granules, tablets, a paste or a beverage. Also, the polymethoxyflavones may be mixed with known formulation additives as necessary.

Known formulation additives include excipients, bases, binders, disintegrators, disintegrating aids, lubricants, fluidizers, coating agents, plasticizers, antifoaming agents, sugar coatings, coatings, gloss agents, foaming agents, moisture-proof agents, surfactants, solubilizing agents, buffering agents, solubilizers, dissolving aids, solvents, stabilizers, emulsifiers, suspending agents, dispersing agents, antioxidants, fillers, viscosity regulators, thickening agents, pH regulators, antiseptic agents, preservatives, sweeteners, taste correctives, refrigerants, flavoring agents, aromatics, aromatic agents, coloring agents and the like.

There may also be combined therewith, DHA (docosahexaenoic acid), EPA (eicosapentaenoic acid), phosphatidylserine, phosphatidylcholine, soybean lecithin, egg yolk lecithin, tocotrienol, GABA (γ-aminobutyric acid), theanine, lycopene, lion's mane mushroom, ginkgo leaf, ashitaba, hop, chrysanthemum, zedoary, saffron, garlic, germinated brown rice, vitamin C, vitamin E, coenzyme Q10, royal jelly, propolis, collagen, phytosterol, vegetable fats and oils (olive oil, soybean oil and the like), unsaturated fatty acids, beeswax, zinc ferment and selenium ferment.

Embodiments of the invention will now be described.

[1] Polymethoxyflavones and their Starting Materials:

The polymethoxyflavones to be extracted and separated according to the invention are compounds represented by the following formula (I):

[Chemical Formula 3]

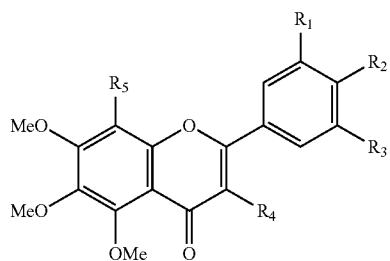

(wherein $R_1$, $R_2$, $R_3$, $R_4$ and $R_5$ each independently represent hydrogen or a methoxy group), and specifically they include pentamethoxyflavone (Mp 179° C.), nobiletin (Mp 134° C.), tetramethoxyflavone (Mp 128° C.), heptamethoxyflavone (Mp 129-131° C.) and tangeretin (Mp 154° C.)

These polymethoxyflavones are abundant in peel oil included in the exocarp of citrus plants. Particularly preferred as starting materials among these, from the viewpoint of availability, are peel oil of sweet orange (*Citrus sinensis*), sour orange (*Citrus aurantium*), tangerine (*Citrus reticlata* Blanco var. *tangerine*), mandarin (*Citrus reticlata* Blanco var. *mandarin*) and shekwasha (*Citrus depressa* Hayata). There are no particular restrictions on the method of obtaining the peel oil, and for example, the method may involve pressing the peel while cold or at ordinary temperature to obtain the peel oil (cold press oil). Also, terpene-cut oil, for example, natural limonene residue industrially produced from orange peel oil, or residue obtained as the low-medium boiling point fraction to serve as an aromatic material, may also be used.

[2] Volatile Component Removal Step

The volatile components in the peel oil are removed by ordinary-pressure or vacuum distillation, but preferably by vacuum distillation from the viewpoint of removing the volatile components at minimally low temperature. The vacuum distillation may be carried out by a common method such as simple distillation, rectification or molecular distillation.

Also, pretreatment to remove the low boiling point components with especially high volatility, such as limonene (bp 175-176° C.) by pre-distillation (preferably under conditions with a pressure of 1000-10,000 Pa and a temperature of 50° C. to 200° C.), before treatment of the obtained residue, i.e. multistage distillation with distillation under high vacuum conditions to thoroughly remove the poorly volatile components remaining in the residue, is preferred from the viewpoint of obtaining a high-purity product.

The distillation in the volatile component removal step is preferably vacuum distillation conducted at a pressure of 1-100 Pa and a distillation temperature of 120° C. to 220° C., and most preferably a pressure of 10-50 Pa and a distillation temperature of 160° C. to 200° C. At below 120° C. it may not be possible to thoroughly remove the volatile components, and at higher than 220° C. some of the polymethoxyflavones will be distilled off.

According to the invention, the volatile components to be removed from the peel oil include hydrocarbon compounds, carbonyl compounds, esters, alcohols and other fragrance components present in peel oil, including limonene, linalool (bp 198° C.), geraniol (bp 229-230° C.), nerol (bp 225-226° C.), α-terpineol (bp 217-218° C.) and citral (bp 229° C.), which are components with higher volatilization degrees, i.e. lower boiling points, than polymethoxyflavones.

[3] Distillation Step by Thin-Film Vacuum Distillation Apparatus

This is a step of using a thin-film vacuum distillation apparatus for further distillation of the residue obtained from distillation removal by the previous volatile component removal step (hereunder referred to as "distillation residue"), to distill out and separate the polymethoxyflavones (hereunder referred to as "distillation residue fraction").

The distillation used in this step is performed by thin-film distillation. Thin-film distillation is a distillation method in which a substance to be distilled (the aforementioned distillation residue) is continuously supplied onto a surface that has been heated to a certain temperature, to form a homogeneous thin-film, and the substance to be distilled is heated while on the surface, volatilizing the volatile components to separate the volatile components and the non-volatile components.

In this step, the pressure and temperature conditions are 0.1-5 Pa, 190-260° C., and preferably 0.4-2 Pa, 190-260° C. A temperature of below 190° C. will require a longer time for distillation of the polymethoxyflavones, while a temperature of above 260° C. will result in distillation of components other than polymethoxyflavones, thereby lowering the polymethoxyflavone content.

[4] Extraction Step by Aqueous Ethanol Solution

This is a step of extracting the previous distillation residue fraction with an aqueous ethanol solution for selective extraction of polymethoxyflavones from the distillation residue.

The ethanol concentration of the aqueous ethanol solution for this step is 10-50% and preferably 20-40%. If the ethanol concentration exceeds 50%, large amounts of contaminants will tend to be extracted with the polymethoxyflavones, and it is preferably not less than 10% because the polymethoxyflavone yield will be reduced.

The amount of aqueous ethanol solution used for this step may be selected as desired, but it is generally preferred to be 1-100 parts by weight and more preferably 2-20 parts by weight of aqueous ethanol solution to 1 part by weight of distillation residue fraction. The extraction temperature may be selected as desired but is preferably between 40° C. and 100° C.

[5] Refining Step with Active Carbon

This is a step of selectively removing the unwanted components from the previous ethanol extract, and especially the residual pesticides, for refining.

The active carbon used for the invention is not particularly restricted so long as it is a type commonly used on an industrial level.

Active carbon is a form of porous carbon with a large area-to-weight ratio and an adsorption capacity, and it is therefore used as an adsorbent. It is activated and produced by a method such as thorough carbonization of a charcoal, coconut shell or coal char starting material, followed by high-temperature treatment with water vapor or impregnation with an aqueous solution of zinc chloride or the like and high-temperature firing. Generally, the area-to-weight ratio is 800-1200 $m^2 \cdot g^{-1}$, the pore volume is 0.2-2 $cm^3 \cdot g^{-1}$ and the pore size is 1-4 nm. The composition of active carbon is mainly carbon, but it also contains small amounts of hydrogen, oxygen and inorganic components, while the chemical structure is based on graphite but it is amorphous and has functional groups such as hydroxyl and quinone groups on the surface.

The active carbon to be used for the invention may be, for example, a commercial product such as Taiko (product of Futamura Chemical Co., Ltd.), Shirasagi (product of Kirin Kyowa Foods Co., Ltd.) or Kuraray Coal (product of Kuraray Chemical Co., Ltd.).

There are no particular restrictions on the conditions for activated carbon treatment in this step, but from the viewpoint of pesticide removal and polymethoxyflavone yield, the amount of active carbon used is preferably 0.01-0.3 part by weight of active carbon with respect to 1 part by weight of polymethoxyflavone, and the treatment temperature is preferably 30° C. to 80° C. From the viewpoint of pesticide removal, formulation stability and polymethoxyflavone yield, for a water-soluble formulation, the amount of active carbon is preferably 0.01-0.3 part by weight of active carbon with respect to 1 part by weight of polymethoxyflavone, the treatment temperature is preferably 30° C. to 80° C., and the processing time is preferably 90 minutes or longer.

The polymethoxyflavones obtained by the manufacturing method described above may be in the form of a mixture of the different polymethoxyflavone compounds, or they may be used as food taste-improving agents or flavor deterioration retarders.

Thus, it is often sufficient for the polymethoxyflavones alone to be separated from the other components in citrus plant peel oil, and it is not always necessary to isolate and purify each of the individual polymethoxyflavone components.

However, when a single high-purity polymethoxyflavone such as heptamethoxyflavone is necessary, it can be easily purified by recrystallization or column chromatography, and when necessary a suitable refining method known among those skilled in the art may be selected for use.

EXAMPLES

The invention will now be explained in greater detail using examples, with the understanding that these examples are merely illustrative and do not limit the scope of the invention in any way.

Measurement Example

Commercially available orange peel oil ("ORANGE PEEL OIL" by Fischer S/A) was diluted 5-fold with ethyl acetate, and the high-performance liquid chromatography (HPLC) procedure described below was used for quantitation of the polymethoxyflavone component content.

The quantitated results are shown below in Table 1. The HPLC conditions used in the experimental examples were as follows.
Apparatus: Agilent 1100 HPLC system by Agilent Technologies Column: "CAPCELL PAK C18 MG" by Shiseido Corp. (column temperature: 40° C.)
Eluent: A. acetonitrile
B. 10% Acetonitrile aqueous solution (pH: 2.5 $H_3PO_4$)
Gradient conditions: 0 minutes→25 minutes
A. Acetonitrile 0% 100%
B. 10% Acetonitrile aqueous solution
(pH 2.5 $H_3PO_4$) 100% 0%
Flow rate: 1 ml/min
Detection wavelength: 325 nm The content of each component was calculated using a calibration curve prepared with a pre-isolated pure product. The polymethoxyflavone contents in Table 1 are the totals of the pentamethoxyflavone, nobiletin, tetramethoxyflavone, heptamethoxyflavone and tangeretin contents.

TABLE 1

| Polymethoxyflavone contents | |
|---|---|
| Compound name | Content (wt %) |
| Pentamethoxyflavone | 0.015 |
| Nobiletin | 0.075 |
| Tetramethoxyflavone | 0.033 |
| Heptamethoxyflavone | 0.075 |
| Tangeretin | 0.045 |
| Polymethoxyflavones | 0.243 |

[Pretreatment]
Commercially available orange peel oil was subjected to vacuum distillation with different distillation systems and pressure conditions, to remove the low boiling point components with particularly high volatility, such as limonene.

The results of analyzing the obtained fraction and distillation residue are shown in Table 2.

The "PMF yields" shown in the table indicate the yields of polymethoxyflavones in the orange peel oils extracted into the tank residues, and they were calculated using the following formula (I).

$$\text{Yield (\%)} = (c \times d)/(a \times b) \times 100(\%) \quad \text{(I)}$$

[Symbols in Formula:
a: Weight of oil used for distillation (kg)
b: Content of polymethoxyflavones in oil used for distillation (%)
c: Weight of distillation residue (kg)
d: Content of polymethoxyflavone(s) in distillation residue (%)]

TABLE 2

| | Distillation system | | | |
|---|---|---|---|---|
| | Precision distillation | Thin-film distillation | Fluidized simple distillation | Simple distillation |
| Pressure | 100-40 Pa | 1000 Pa | 1330 Pa | 1330 Pa |
| Temperature | 125-145° C. | 60° C. | 160° C. | 150° C. |
| PMF content % | | | | |
| Pentamethoxyflavone | 0.42 | 0.35 | 0.54 | 0.04 |
| Nobiletin | 3.19 | 2.71 | 2.88 | 2.29 |
| Tetramethoxyflavone | 1.35 | 1.15 | 1.12 | 0.31 |
| Heptamethoxyflavone | 3.17 | 2.69 | 2.32 | 2.36 |
| Tangeretin | 2.18 | 1.87 | 1.80 | 0.99 |
| Total PMF | 10.32 | 8.77 | 8.66 | 5.99 |
| PMF recovery rate | 100% | 98% | 100% | 97% |

*PMF: Polymethoxyflavone

As seen by the results in Table 2, the pretreatment removal step for fragrance components allowed quantitative yields of polymethoxyflavones regardless of the distillation system, and allowed preparation of polymethoxyflavones as functional materials from the waste resulting from extraction of beneficial fragrance components from Rutaceae plants, demonstrating that the technology is highly economical.

Distillation Example

A 100 g portion of tank residue obtained from pretreatment distillation was subjected to vacuum distillation with different temperature and pressure conditions, for removal of the volatile components.

The results of analyzing the obtained fraction and distillation residue are shown in Table 3.

The "yields" in the table represent the weights of the fractions and distillation residues obtained by vacuum distillation, as percentages of the weights of the tank residues from the pretreatment distillation, and the polymethoxyflavone yields represent the yields of polymethoxyflavones in the orange peel oils extracted into the tank residues, and were calculated by the following formula (I).

$$\text{Yield (\%)} = (c \times d)/(a \times b) \times 100(\%) \quad (I)$$

[Symbols in Formula:
a: Weight of oil used for distillation (kg)
b: Content of polymethoxyflavones in oil used for distillation (%)
c: Weight of distillation residue (kg)
d: Content of polymethoxyflavone(s) in distillation residue (%)]

A 500 g portion of 30% aqueous ethanol solution was added to 25 g of the distillation residue obtained by distillation, and the mixture was heated to reflux for 1 hour for extraction. After cooling to 25° C., the upper layer oil portion and the aqueous ethanol solution layer were separated. The aqueous ethanol solution layer was filtered, and then the polymethoxyflavones obtained by concentration to dryness under reduced pressure were diluted to 1% with a 50% aqueous ethanol solution, the dilute solution was added to a 10% aqueous solution of glucose to a concentration of 0.1%, and the presence or absence of off-taste and off-odor was evaluated, with the results shown in Table 3.

TABLE 3

Results for distillation example

| Distillation conditions | | Fraction | | Distillation residue | | |
|---|---|---|---|---|---|---|
| Pressure reduction (Pa) | Temperature (° C.) | Yield (%) | Recovery rate (%) | Yield (%) | Recovery rate (%) | Off-taste and off-odor |
| 10 | 120 | 35 | 0 | 63 | 98 | Orange-like off-odor |
| 10 | 140 | 41 | 0 | 58 | 98 | Orange-like off-odor |
| 100 | 160 | 38 | 0 | 60 | 97 | Orange-like off-odor |
| 50 | 160 | 43 | 3 | 55 | 93 | No off-taste/off-odor |
| 10 | 180 | 46 | 7 | 53 | 92 | No off-taste/off-odor |
| 50 | 200 | 48 | 6 | 50 | 93 | No off-taste/off-odor |
| 10 | 200 | 50 | 9 | 48 | 89 | No off-taste/off-odor |
| 100 | 220 | 49 | 8 | 50 | 88 | Distillation off-odor |
| 50 | 220 | 53 | 20 | 46 | 77 | Distillation off-odor |
| 10 | 220 | 56 | 41 | 40 | 55 | Distillation off-odor |

As shown in Table 3, a distillation temperature of higher than 200° C. resulted in run-off of the polymethoxyflavones into the fraction, and reduced the polymethoxyflavone yield in the distillation residue. On the other hand, a distillation temperature of 160° C. or lower resulted in residual orange aroma.

Example 1

(1) Volatile Component Removal Step

A 1000 kg portion of the commercially available orange peel oil used in the measurement example was subjected to vacuum distillation at a pressure of 1330 Pa and a tank temperature of 150° C., as pretreatment, and there was obtained 50 kg of tank residue from which the low-boiling-point components such as limonene were removed.

A 50 kg portion of the tank residue obtained in the pretreatment was subjected to distillation using a thin-film distillation apparatus ("CEH-400BII" by Ulvac Techno, Ltd.) at a pressure of 40 Pa and a temperature of 190° C., and there was obtained 25.6 kg of a distillation residue from which the poorly volatile components were removed.

The obtained distillation residue was diluted 1000-fold with ethyl acetate, and measured under the same conditions as the measurement example. The results are shown in Table 4.

The yields indicate the yields of polymethoxyflavones in the orange peel oils extracted into the distillation residues, and they were calculated using the following formula (I).

$$\text{Yield (\%)} = (c \times d)/(a \times b) \times 100(\%) \quad (I)$$

[Symbols in Formula:
a: Weight of oil used for distillation (kg)
b: Content of polymethoxyflavones in oil used for distillation (%)
c: Weight of distillation residue (kg)
d: Content of polymethoxyflavone(s) in distillation residue (%)]

TABLE 4

Results for volatile component removal step

| Compound name | Content (wt %) | Recovery rate (wt %) |
|---|---|---|
| Pentamethoxyflavone | 0.56 | 95.7 |
| Nobiletin | 2.92 | 99.8 |
| Tetramethoxyflavone | 1.26 | 97.9 |
| Heptamethoxyflavone | 2.91 | 99.5 |
| Tangeretin | 1.74 | 99.1 |
| Polymethoxyflavones | 9.39 | 99.1 |

As shown in Table 4, the volatile component removal step resulted in recovery of the polymethoxyflavones into the distillation residue from the orange peel oil without loss. The following polymethoxyflavone separating step was carried out using the distillation residue obtained from the volatile component removal step described above.

Example 2

(2) Distillation Step by Thin-Film Vacuum Distillation Apparatus

A 150 g portion of the distillation residue obtained from the volatile component removal step was subjected to distillation using a thin-film vacuum distillation apparatus ("MS-F" by Taika Industry Co., Ltd.) at a pressure of 2 Pa and a temperature of 210° C., and 56 g of polymethoxyflavones was obtained. The obtained polymethoxyflavones were in the form of an orange, highly viscous pasty oil.

The polymethoxyflavones obtained in this manner were diluted 1000-fold with a 99.5% alcohol aqueous solution, and the polymethoxyflavone content in the solid portion was measured under the same conditions as the measurement example, with the results shown in Table 5. The yield represents the yield of polymethoxyflavone(s) from the distillation residue obtained by the pretreatment distillation, and it was calculated in the same manner as calculation of the yield in the volatile component removal step.

TABLE 5

Results for distillation step by thin-film vacuum distillation apparatus

| Compound name | Content (wt %) | Recovery rate (wt %) |
|---|---|---|
| Pentamethoxyflavone | 1.49 | 99.3 |
| Nobiletin | 7.75 | 99.1 |
| Tetramethoxyflavone | 3.35 | 99.3 |
| Heptamethoxyflavone | 7.74 | 99.9 |
| Tangeretin | 4.66 | 100 |
| Polymethoxyflavones | 24.99 | 99.3 |

As shown in Table 5, it was possible to easily obtain a polymethoxyflavone composition with high content, at a high yield.

Example 3

(1) Volatile Component Removal Step

Exactly the same procedure was carried out as the volatile component removal step of Example 1, to obtain 25.6 kg of a distillation residue with the volatile components removed.

(2) Distillation Step by Thin-Film Vacuum Distillation Apparatus

A 100 g portion of the obtained distillation residue was subjected to thin-film vacuum distillation under different temperature conditions, with the pressure set to 0.4 Pa. Table 6 shows the results of analyzing the obtained fraction under the same conditions as Example 1. The yield represents the weight of the fraction obtained by vacuum distillation as a percentage of the weight of the tank residue in the volatile component removal step, and the yield of polymethoxyflavones was calculated by the same method as the yield in the volatile component removal step.

TABLE 6

Results for distillation step by thin-film vacuum distillation apparatus

| Distillation temperature (° C.) | Content (%) | Recovery rate (%) |
|---|---|---|
| 170 | 27.7 | 81.7 |
| 190 | 26.9 | 91.8 |
| 230 | 25.1 | 99.3 |
| 260 | 22.8 | 98.9 |
| 280 | 18.9 | 99.7 |

As shown in Table 6, a distillation temperature of higher than 260° C. resulted in run-off of the components other than the polymethoxyflavones, and reduced the polymethoxyflavone content. On the other hand, a distillation temperature of 190° C. or lower resulted in a reduced polymethoxyflavone yield.

Example 4

Extraction Step by Aqueous Ethanol Solution

After adding 100 g of an aqueous ethanol solution to 10 g of the polymethoxyflavones obtained in Example 2, the mixture was heated to 60° C. and stirred and extracted for 1 hour. After cooling to −15° C., the upper layer oil portion and the aqueous ethanol solution layer were separated, and the aqueous ethanol solution layer was filtered. The obtained polymethoxyflavones were analyzed under the same conditions as Example 1, with the results shown in Table 7. The content in the table represents the proportion of polymethoxyflavones with respect to the oil dissolved in the aqueous ethanol solution.

TABLE 7

Extraction step by aqueous ethanol solution

| Ethanol content (%) | Content (%) | Recovery rate (%) |
|---|---|---|
| 10 | 86.7 | 33.1 |
| 20 | 87.5 | 60.2 |
| 30 | 86.7 | 78.6 |
| 40 | 82.7 | 88.3 |
| 50 | 73.5 | 94.6 |
| 60 | 64.4 | 97.1 |
| 70 | 52.3 | 97.9 |
| 80 | 41.2 | 98.7 |
| 90 | 30.6 | 94.2 |
| 99.5 | 25.5 | 97.6 |

According to the results shown in Table 7, using an ethanol concentration of 10% for extraction resulted in high purity of separated polymethoxyflavones, but was inefficient with a low yield of 33%.

On the other hand, using an ethanol concentration of 60% or greater resulted in a high yield of 97-99% for separated polymethoxyflavones, but a low purity of 25-64%.

Example 5

Refining Step with Active Carbon

A 100 g portion of the extract obtained using 40 wt % ethanol in Example 4 was heated to 60° C., 0.1 g of active carbon ("Taiko" by Futamura Chemical Co., Ltd.) (4 wt % with respect to the polymethoxyflavones) was added and stirred therewith, and then the supernatant was sampled and filtered with a 0.45 μm membrane filter, and the polymethoxyflavones in the obtained filtrate were analyzed under the same conditions as in Example 1, with the results shown in Table 8. The yields in Table 8 represent the polymethoxyflavone yields in the activated carbon treatment step.

TABLE 8

Polymethoxyflavone recovery rate by active carbon treatment step

| | Treatment time (min) | | | | |
|---|---|---|---|---|---|
| | 0 | 60 | 90 | 120 | 150 |
| Recovery rate (%) | 100 | 86 | 100 | 100 | 100 |

According to the results in Table 8, an active carbon treatment time of 90 minutes or longer allowed recovery of polymethoxyflavones without loss.

Example 6

After concentrating the extract obtained using 30 wt % ethanol in Example 4, ethanol and water were added to prepare an extract with a composition of 10% polymethoxyflavones, 20% water and 30% ethanol.

A 100 g portion of the obtained extract was heated to 50° C., and active carbon ("Taiko" by Futamura Chemical Co., Ltd.) was added and stirred therewith for 120 minutes, after which the mixture was filtered with Celite to obtain an activated carbon treatment solution.

The obtained filtrate was kept in the dark at room temperature for 1 day, and the presence or absence of precipitation was confirmed.

The polymethoxyflavones in the filtrate were analyzed under the same conditions as Example 1, with the results shown in Table 9. The yields in Table 9 represent the polymethoxyflavone yields in the activated carbon treatment step.

TABLE 9

Active carbon amounts used

| | Active carbon used (wt % of PMF) | | | | |
|---|---|---|---|---|---|
| | 0 | 5 | 10 | 20 | 40 |
| PMF recovery rate (%) | 100 | 99 | 98 | 96 | 88 |
| Precipitation | + | − | − | − | + |

As shown in Table 9, a precipitate formed with time when no active carbon was used, but when active carbon was used at 5-20 wt % with respect to the polymethoxyflavones, a solution with stability over time was obtained at a high yield.

On the other hand, when active carbon was used at 40% with respect to the polymethoxyflavones, the polymethoxyflavone yield was reduced and a precipitate formed with time.

Example 7

A 100 g portion of the extract obtained with 40 wt % ethanol in Example 4 was adjusted to a temperature of 5° C. or 50° C., and then 1 g of active carbon (10 wt % with respect to the polymethoxyflavones) was added and stirred therewith for 120 minutes, and filtered with Celite to obtain an activated carbon treatment solution.

The obtained filtrate was kept in the dark at room temperature for 1 day, and the presence or absence of precipitation was confirmed.

The polymethoxyflavones in the filtrate were analyzed under the same conditions as Example 1, with the results shown in Table 10. The yields in Table 10 represent the polymethoxyflavone yields in the activated carbon treatment step.

TABLE 10

Active carbon treatment temperature

| | Treatment temperature (° C.) | |
|---|---|---|
| | 5 | 50 |
| PMF recovery rate(%) | 100 | 100 |
| Precipitation | + | − |

As shown in Table 10, activated carbon treatment at 50° C. allowed a highly stable filtrate to be obtained without loss of polymethoxyflavones. On the other hand, treatment at 5° C. did not result in loss of polymethoxyflavones, but the stability was not improved.

[Residual Pesticide Reduction Test]
(1) Preparation of Sample for Residual Pesticide Analysis
(a) Thin-Film Distillation Fraction Medium chain fatty acid triglycerides were added to the fraction obtained by the distillation step with a thin-film vacuum distillation apparatus in Example 2, to prepare a 10% polymethoxyflavone solution.

(b) Activated Carbon Treatment Solution

After adding 500 g of a 40 wt % aqueous ethanol solution to 50 g of the fraction obtained by the distillation step with a thin-film vacuum distillation apparatus in Example 2, the mixture was heated to 60° C. and stirred for 60 minutes for extraction.

After cooling to −15° C., the aqueous ethanol solution layer was filtered to obtain a filtrate.

A 100 g portion of the extract obtained in this manner was heated to 50° C., 0.25 9 of active carbon ("Taiko" by Futamura Chemical Co., Ltd.) (10 wt % with respect to the polymethoxyflavones) was added and stirred therewith for 120 minutes, and the mixture was filtered with Celite and concentrated, after which ethanol and water were added to prepare an extract with a 10% polymethoxyflavone content, and the residual pesticides in the solution were analyzed.

The residual pesticide analysis results are shown in Table 11. The values in Table 11 represent the concentrations in the residual pesticide analysis sample (ppm). The residual pesticide analysis was performed by the Food Analysis Technology Center (SUNATEC), with simultaneous analysis of 200 components.

TABLE 11

Residual pesticide analysis results

| Pesticide name | Thin-film fraction | Active carbon-treated solution |
|---|---|---|
| Chlorobenzilate | 0.2 | Undetected |
| Cypermethrin | 0.2 | Undetected |
| Dicofol* | 5.5 | 0.4 |
| Tetradifon | 0.15 | Undetected |
| Triazophos | 0.2 | Undetected |
| Bifenthrin | 0.4 | Undetected |
| Pyridaphenthion | 0.25 | 0.1 |
| Fenpropathrin | 0.2 | Undetected |
| Bromopropylate | 5.5 | 0.3 |
| Propargite | 10 | Undetected |
| Methidathion | 0.65 | 0.1 |

*Alternate name: Kelthane

As shown in Table 11, residual pesticides remained in the thin-film distillation fraction, but extraction with the aqueous ethanol solution and treatment with active carbon greatly reduced or eliminated the residual pesticides.

Example 8

Oil-Soluble Formulation

A 740 g portion of the filtrate obtained by activated carbon treatment at 50° C. in Example 7 was concentrated to remove the water and ethanol, and then medium chain fatty acid triglycerides were added to obtain 140 g of an oil-soluble formulation with a polymethoxyflavone content of 10%.

The oil-soluble formulation obtained in this manner was a highly fluid liquid composition, and a highly stable formulation.

Example 9

The oil-soluble formulation obtained in Example 8 was used to prepare a soft capsule food having the composition shown in Table 12 below, by a common method.

TABLE 12

| Soft capsule food | |
|---|---|
| Added components | Weight (g) |
| Oil-soluble formulation of Example 8 | 20.0 |
| Olive oil | 30.0 |
| Bees wax | 15.0 |
| DHA | 10.0 |
| EPA | 1.5 |
| Egg yolk lecithin | 10.0 |
| Ginkgo leaf extract | 3.0 |
| Phosphatidyl serine | 4.0 |
| GABA | 1.5 |
| Vitamin E | 5.0 |
| Total | 100.0 |

Example 10

Preparation of Water-Soluble Formulation

Polymethoxyflavones of the invention were used to prepare a water-soluble formulation in the following manner.

A 99 g portion of the solution obtained by activated carbon treatment at 50° C. in Example 7 was concentrated and ethanol was added to adjust the polymethoxyflavone concentration to 10%, to obtain 21 g of an ethanol formulation.

The water-soluble formulation obtained in this manner had no off-taste or off-odor, and was a low-viscosity yellow liquid, and a highly stable formulation.

Example 11

Preparation of Orange Beverage

An orange beverage was prepared with the formulation shown in Table 13.

TABLE 13

| Orange beverage | |
|---|---|
| Added components | Weight (g) |
| Orange concentrated juice Bx64 | 62.3 |
| High-fructose corn syrup | 76.7 |
| Citric acid | 1.3 |
| Vitamin C | 0.05 |
| Aqueous formulation of Example 9 | 0.3 |
| Water | Remainder |
| Total | 1000 |

The beverage was evaluated to be a palatable beverage with no noticeable off-taste or off-odor.

Example 12

Emulsified Powder Formulation

After heating and dissolving 1 part by weight of gum arabic in 9 parts by weight of water, the mixture was added to the water-soluble formulation obtained in Example 10 and concentrated to remove the ethanol, after which it was spray-dried to prepare an emulsified powder formulation comprising 10% polymethoxyflavones. The powder formulation was fluid and was a highly stable formulation.

Example 13

The powder formulation obtained in Example 12 was used to prepare tablets having the composition shown in Table 14 below, by a common method.

TABLE 14

| Tablets | |
|---|---|
| Added components | Weight (g) |
| Powdered formulation of Example 12 | 50.0 |
| Starch | 30.0 |
| Cellulose | 15.0 |
| Glycerin fatty acid ester | 3.0 |
| Silicon dioxide | 2.0 |
| Total | 100.0 |

The tablets were evaluated as being edible without any noticeable off-taste or off-odor.

INDUSTRIAL APPLICABILITY

According to the invention it is possible to combine refining by distillation (especially vacuum distillation) and reduced pressure thin-film distillation with extraction by an aqueous ethanol solution and activated carbon treatment, to conveniently and very efficiently separate polymethoxyflavones from citrus plant peel oil, with low impurities such as residual pesticides and without off-taste or off-odor. In addition, the invention allows inexpensive and highly safe polymethoxyflavones, that are useful in food products, to be obtained on an industrial scale. Furthermore, application of the invention allows utilization of orange peel oil residue after extraction of terpenes such as limonene and essential oil (terpeneless oil) from which the terpenes have been removed, which are materials that have been discarded in the prior art, and it can provide a major contribution to effective utilization of resources.

The invention claimed is:

1. A method for manufacturing a polymethoxyflavone, the method comprising:
   (1) distilling a citrus plant peel oil under a pressure of 1 Pa to 100 Pa and at a temperature of 120° C. to 220° C. and thereby removing at least one volatile component to obtain a distillation residue (1);
   (2) distilling the distillation residue (1) with a thin-film vacuum distillation apparatus under a pressure of 0.1 Pa to 5 Pa and at a temperature of 190° C. to 260° C. to obtain a fraction (2);
   (3) extracting the fraction (2) with an aqueous ethanol solution to obtain an extract (3); and
   (4) after removing at least one insoluble oil, contacting the extract (3) with an active carbon to produce at least one polymethoxyflavone of formula (I):

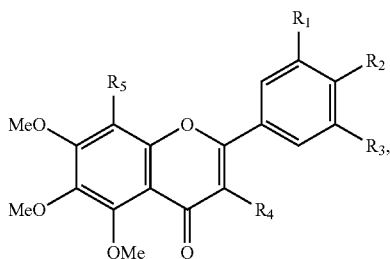

wherein:

R₁, R₂, R₃, R₄ and R₅ each independently represent hydrogen or a methoxy group; and the at least one polymethoxyflavone is highly stable over time and has a reduced residual pesticide level relative to polymethoxyflavones produced without the extracting (3) and the contacting (4).

2. The method of claim 1, wherein the citrus plant peel oil is a terpene-cut product.

3. The method of claim 2, wherein the distilling (1) occurs under a pressure of 10 Pa to 50 Pa and at a temperature of 160° C. to 200° C.

4. The method of claim 2, wherein the distilling (2) with a thin-film vacuum distillation apparatus occurs under a pressure of 0.4 to 2 Pa and at a temperature of 190° C. to 260° C.

5. The method of claim 2, wherein the aqueous ethanol solution has an ethanol concentration of 10-50%.

6. The method of claim 2, wherein a citrus plant from which the citrus plant peel oil is obtained is at least one selected from the group consisting of sweet orange (*Citrus sinensis*), sour orange (*Citrus aurantium*), tangerine (*Citrus reticlata* Blanco var. tangerine), mandarin (*Citrus reticlata* Blanco var. mandarin) and shekwasha (*Citrus depressa* Hayata).

7. The method of claim 2, wherein the polymethoxyflavone is at least one selected from the group consisting of pentamethoxyflavone, nobiletin, tetramethoxyflavone, tangeretin and heptamethoxyflavone.

8. The method of claim 1, wherein the distilling (1) occurs under a pressure of 10 Pa to 50 Pa and at a temperature of 160° C. to 200° C.

9. The method of claim 1, wherein the distilling (1) comprises:
(1a) pre-distilling the citrus plant peel oil under a pressure of 1000 Pa to 10,000 Pa and at a temperature of 50° C. to 200° C. to obtain a residue (1a); and then
(1b) distilling the residue (1a) under a pressure of 1 Pa to 100 Pa and at a temperature of 120° C. to 220° C. to obtain the distillation residue (1).

10. The method of claim 1, wherein the distilling (2) with a thin-film vacuum distillation apparatus occurs under a pressure of 0.4 to 2 Pa and at a temperature of 190° C. to 260° C.

11. The method of claim 1, wherein the aqueous ethanol solution has an ethanol concentration of 10-50%.

12. The method of claim 1, wherein a citrus plant from which the citrus plant peel oil is obtained is at least one selected from the group consisting of sweet orange (*Citrus sinensis*), sour orange (*Citrus aurantium*), tangerine (*Citrus reticlata* Blanco var. tangerine), mandarin (*Citrus reticlata* Blanco var. mandarin) and shekwasha (*Citrus depressa* Hayata).

13. The method of claim 1, wherein the polymethoxyflavone is at least one selected from the group consisting of pentamethoxyflavone, nobiletin, tetramethoxyflavone, tangeretin and heptamethoxyflavone.

* * * * *